US011419632B2

(12) United States Patent
Kunis (10) Patent No.: US 11,419,632 B2
(45) Date of Patent: *Aug. 23, 2022

(54) TRANSSEPTAL ACCESS DEVICE AND METHOD OF USE

(71) Applicant: Mark D. Wieczorek, San Diego, CA (US)

(72) Inventor: Christopher Gerard Kunis, Escondido, CA (US)

(73) Assignee: Mark D. Wieczorek, P.C., San Diego, CA (US)

( * ) Notice: Subject to any disclaimer, the term of this patent is extended or adjusted under 35 U.S.C. 154(b) by 645 days.

This patent is subject to a terminal disclaimer.

(21) Appl. No.: 16/429,349

(22) Filed: Jun. 3, 2019

(65) Prior Publication Data

US 2019/0282781 A1 Sep. 19, 2019

Related U.S. Application Data

(60) Continuation of application No. 14/567,427, filed on Dec. 11, 2014, now Pat. No. 10,307,569, which is a (Continued)

(51) Int. Cl.
*A61B 17/34* (2006.01)
*A61M 25/00* (2006.01)
(Continued)

(52) U.S. Cl.
CPC ..... *A61B 17/3478* (2013.01); *A61M 25/0082* (2013.01); *A61B 2017/00247* (2013.01); *A61B 2017/306* (2013.01)

(58) Field of Classification Search
CPC . A61M 5/00; A61M 25/0082; A61B 1/00089; A61B 2017/306; A61B 17/3478;
(Continued)

(56) References Cited

U.S. PATENT DOCUMENTS 4,222,380 A 9/1980 Terayama
4,662,736 A 5/1987 Belanger
(Continued)

FOREIGN PATENT DOCUMENTS

WO 2007017060 A2 12/2001
WO 2003077733 A2 9/2003
(Continued)

OTHER PUBLICATIONS

Raymond W. Sy et al., "Troubleshooting Difficult Transseptal Catheterization", Journal of Cardiovascular Electrophysiology, Nov. 2010, pp. 1-5.
(Continued)

*Primary Examiner* — Katherine M Shi
(74) *Attorney, Agent, or Firm* — Mayer & Williams, PC (57) ABSTRACT

Systems, devices, and methods are provided for transseptal access of septa within a patient. The device can be advanced to a septum, e.g., towards a fossa ovalis. Instead of applying positive pressure to "tent" the septum, a negative pressure is applied to a lumen within a sheath, e.g., within an elongated member slidable within the sheath, via a negative pressure source such as a syringe on the proximal end of the sheath. This results in the septum pulling inward. The sheath employs a stationary needle-like central core component contained within the lumen of the sheath that punctures the septum when the same is pulled passed it by the negative pressure. The stationary needle-like central core component may be hollow and may form a portion of the elongated member or may be coupled to a distal end thereof.

16 Claims, 6 Drawing Sheets

Related U.S. Application Data division of application No. 13/093,546, filed on Apr. 25, 2011, now Pat. No. 8,940,008.

(60) Provisional application No. 61/443,483, filed on Feb. 16, 2011, provisional application No. 61/639,674, filed on Jun. 29, 2010, provisional application No. 61/327,542, filed on Apr. 23, 2010.

(51) Int. Cl.
*A61B 17/00* (2006.01)
*A61B 17/30* (2006.01)

(58) Field of Classification Search
CPC ......... A61B 1/0008; A61B 1/018; A61B 1/04; A61B 2017/00247
See application file for complete search history.

(56) References Cited

U.S. PATENT DOCUMENTS

| | | | |
|---|---|---|---|
| 4,807,625 A | 2/1989 | Singleton | |
| 6,152,144 A | 11/2000 | Lesh et al. | |
| 6,156,018 A | 12/2000 | Hassett | |
| 7,056,294 B2 | 6/2006 | Khairkhahan et al. | |
| 7,257,450 B2 | 8/2007 | Auth et al. | |
| 7,678,081 B2 | 3/2010 | Whiting et al. | |
| 7,850,685 B2 | 12/2010 | Kunis et al. | |
| 7,860,555 B2 | 12/2010 | Saadat | |
| 7,860,556 B2 | 12/2010 | Saadat | |
| 8,021,359 B2 | 9/2011 | Auth et al. | |
| 8,075,532 B2 | 12/2011 | Kassab et al. | |
| 8,480,708 B2 | 7/2013 | Kassab et al. | |
| 8,540,674 B2 | 9/2013 | Kassab et al. | |
| 8,647,367 B2 | 2/2014 | Kassab et al. | |
| 8,876,776 B2 | 11/2014 | Kassab et al. | |
| 9,050,064 B2 | 6/2015 | Kassab et al. | |
| 2002/0169377 A1 | 11/2002 | Khairkhahan et al. | |
| 2003/0130626 A1* | 7/2003 | VanTassel | A61M 5/3286 604/272 |
| 2004/0098031 A1 | 5/2004 | Van der Burg et al. | |
| 2005/0113860 A1 | 5/2005 | Keidar | |
| 2006/0200119 A1 | 9/2006 | Vaska et al. | |
| 2007/0287886 A1 | 12/2007 | Saadat | |
| 2007/0293724 A1 | 12/2007 | Saadat et al. | |
| 2008/0004485 A1 | 1/2008 | Moreschi | |
| 2008/0009859 A1 | 1/2008 | Auth et al. | |
| 2008/0009886 A1 | 1/2008 | Self | |
| 2008/0015445 A1 | 1/2008 | Saadat et al. | |
| 2008/0015569 A1 | 1/2008 | Saadat et al. | |
| 2008/0033290 A1 | 2/2008 | Saadat et al. | |
| 2008/0039897 A1 | 2/2008 | Kluge et al. | |
| 2008/0214889 A1 | 9/2008 | Saadat et al. | |
| 2009/0182326 A1 | 7/2009 | Zenati et al. | |
| 2009/0227999 A1 | 9/2009 | Willis et al. | |
| 2010/0004506 A1 | 1/2010 | Saadat | |
| 2010/0022822 A1 | 1/2010 | Walshe | |
| 2010/0191279 A1 | 7/2010 | Kassab et al. | |
| 2011/0060182 A1 | 3/2011 | Kassab et al. | |
| 2011/0144572 A1 | 6/2011 | Kassab | |
| 2012/0191181 A1 | 7/2012 | Kassab et al. | |
| 2016/0339210 A9 | 11/2016 | Kassab et al. | |
| 2017/0080218 A9 | 3/2017 | Kassab et al. | |

FOREIGN PATENT DOCUMENTS

| | | |
|---|---|---|
| WO | 2006060019 A1 | 6/2006 |
| WO | 2008/010905 A2 | 1/2008 |
| WO | 2008/091612 A2 | 7/2008 |
| WO | 2008121278 A2 | 10/2008 |
| WO | 2008/134104 A2 | 11/2008 |
| WO | 2008/134128 A1 | 11/2008 |
| WO | 2009072114 A2 | 6/2009 |
| WO | 2009/094237 A1 | 7/2009 |
| WO | 2009099464 A1 | 8/2009 |

OTHER PUBLICATIONS

Robert De Ponti et al., "Trans-Septal Catheterization in the Electrophysiology Laboratory: Data From a Multicenter Survey Spanning 12 Years", Journal of the American College of Cardiology, vol. 47, No. 5, 2006, http://www.content.onlinejacc.org/cgi/content/full/47/5/1037.
U.S. Appl. No. 60/881,831.
U.S. Appl. No. 60/914,452.
U.S. Appl. No. 60/817,421.

* cited by examiner

TRANSSEPTAL ACCESS DEVICE AND METHOD OF USE

CROSS-REFERENCE TO RELATED APPLICATIONS

This application is a continuation of U.S. application Ser. No. 14/567,427, filed Dec. 11, 2014, which is a Divisional of Ser. No. 13/093,546, filed Apr. 25, 2011, entitled "TRANSSEPTAL ACCESS DEVICE AND METHOD OF USE"; which claims benefit of priority of U.S. Provisional Patent Applications: Ser. No. 61/327,542, filed Apr. 23, 2010, entitled "TRANSSEPTAL ACCESS DEVICE AND METHOD OF USE"; Ser. No. 61/359,674, filed Jun. 29, 2010, entitled "TRANSSEPTAL ACCESS DEVICE AND METHOD OF USE; and Ser. No. 61/443,483, filed Feb. 16, 2011, entitled "TRANSSEPTAL ACCESS DEVICE AND METHOD OF USE"; all of the above are herein incorporated by reference in their entirety.

BACKGROUND

In many cardiac procedures, it is necessary to obtain access through the cardiac septum. For example, in treating atrial fibrillation, it is often necessary to isolate the electrical pathways from the PVs ("PVs"), which are located on the posterior wall of the left atrium ("LA"). As all other veins from the body lead to the right atrium, in order to get to the LA, catheters must get across the atrial septum. This is done by piercing a small hole in the septal wall, typically at a location called the fossa ovalis ("FO"). Such access is termed transseptal ("TS") access. Once in the LA, the physician may perform a procedure to electrically isolate the PVs from the LA.

In more detail, TS access is performed by delivering a sheath/dilator thru the venous bed into the right atria along the septal wall. With the tip of the dilator dragged along the septal wall, the same is dragged to the location of the FO. The sheath is then slightly advanced forward, applying pressure to the FO, creating what is called "tenting" of the FO. A long TS needle (e.g., a "Brockenbrough" or "BB" needle) is then advanced thru the lumen of the dilator that is inserted thru the sheath. The needle is advanced against the FO while it is tented. The needle then punctures thru the FO and into the LA.

The TS needle may be hollow or may incorporate a guidewire lumen to enable a guidewire to be threaded through and into the LA of the heart. Once the guidewire is passed through the TS needle and into the LA, the needle, dilator and sheath are retracted while the guidewire remains in the LA.

In about 20% of TS cases, there is difficulty obtaining TS access because, as the physician pushes the sheath forward with the needle, both slide up or down instead of moving forward, increasing the tension on the FO, causing the same to tent while the needle penetrates the tissue. In other cases, if the septum is heavily fibrotic, significant pressure is required to advance the TS needle into the LA. Both cases occasionally cause puncture of the opposite wall by a sudden exertion of the needle through the septum and subsequent perforation, causing a severe adverse event and potential for death.

SUMMARY

The current invention provides a system and method for achieving TS access while minimizing complications associated with obtaining TS access. In one implementation, the system includes a device that at least in part replaces the dilator and/or the needle. The device has a flared distal end, e.g., with a funnel-shaped polymer element that is radiopaque attached to the distal portion of a dilator element or needle, and within the flared distal end, a vacuum, suction, or other negative pressure may be applied. Also within the flared distal end is a center core section equipped with a pointed feature like a needle. With the use of a syringe or other source of negative pressure connected to the proximal end of the device, negative pressure is applied and the funnel tip prolapses, pulling the FO towards the stationary needle feature, puncturing the FO and obtaining access to the LA. A guidewire may then be advanced through a hollow portion of the puncturing feature of the TS access device for subsequent procedures.

In one aspect, the invention is directed to a method of gaining access through a septum, including: delivering a device to a selected location at a septum, the device including a funnel with a proximal end and a distal end and an interior therebetween, the distal end having a greater radius than the proximal end; placing the distal end of the funnel against the selected location; drawing a negative pressure in the interior, such that a portion of the septum and selected location are pulled within the interior of the device; and continuing to draw a negative pressure in the interior until an indication is received that the septum has been pulled past a stationary needle disposed within the interior.

Implementations of the invention may include one or more of the following. Upon receipt of the indication, the negative pressure may be increased to zero or a lumen in which the negative pressure was drawn may be valved off. The drawing a negative pressure may include coupling a syringe to a lumen, the lumen in pressure communication with the interior, and pulling back on a plunger of the syringe. The selected location may be a fossa ovalis. The negative pressure drawn may be between about that drawn by a 5 cc syringe and that drawn by a 100 c syringe, and even more between about that drawn by a 10 cc syringe and that drawn by a 20 cc syringe. The indication may be a presence of blood in a lumen in which the negative pressure was drawn or a reduction in the amount of negative pressure drawn. The method may further include inserting a guide wire through the device such that a distal tip of the guide wire is disposed in a desired location of the heart.

In another aspect, the invention is directed to a non-transitory computer readable medium, comprising instructions for causing a computing device to perform the above method.

In yet another aspect, the invention is directed to a device for transseptal access, including: an elongated member having a proximal end and a distal end, and a piercing element disposed at the distal end; and a funnel coupled to the elongated member at the distal end, the funnel having a proximal end with a first radius and a distal end with a second radius, the second radius greater than the first radius, the funnel having a retracted configuration and an expanded configuration, the expanded configuration defining an interior; and the device is such that the elongated member, the needle, and the funnel are configured to be delivered to a septal location through a transseptal sheath, and such that upon removal of the funnel from the sheath, the funnel assumes the expanded configuration, and such that a pressure lumen is defined in the elongated member extending from the proximal end and into the interior of the funnel.

Implementations of the invention may include one or more of the following. The first radius may be between about 3 French to 10 French, and the second radius may be between about 2.5 mm to 15 mm. Even more, first radius may be between about 5 French to 8 French, and the second radius may be between about 5 mm to 10 mm. The device may further include a fitting attached to the pressure lumen at the proximal end of the elongated member, the fitting configured to attach a negative pressure source thereto. The fitting may be configured to attach a syringe thereto. The funnel may further comprise a lip formed at the distal end. The negative pressure source may be configured to draw a negative pressure of between about that drawn by a 5 cc syringe and that drawn by a 100 c syringe, and even more between about that drawn by a 10 cc syringe and that drawn by a 20 cc syringe. The funnel may further include a rib, a spine member, or a pleat. The spine member may be attached to the funnel or not. The funnel may have a straight shape or a convoluted shape. The elongated member may have further defined a guidewire lumen therein, the guidewire lumen extending from the proximal end and into the interior of the funnel. In the retracted configuration, the funnel may substantially surround the stationary needle. In the expanded configuration, the funnel distal end may extend further in a distal direction than does the piercing element. The piercing element may be a stationary needle coupled to the elongated member at the distal end. The piercing element may be a dilator with a sharp tip. The funnel may be formed of a shape memory material, such as a polymer, and the rib or spine member may be comprised of a shape memory metal. The shape memory metal may be nitinol.

Advantages of the invention may include one or more of the following. The chance of puncture of cardiac walls is reduced by pulling in the FO with the negative pressure towards a stationary needle. This system may be combined with other devices, e.g., with a needle tip that curls after puncture, for an especially safe procedure. Another safety feature is that during delivery of the TS Access device, the funnel-shaped polymer element may be caused to collapse around the needle or penetrating, piercing, or puncturing element during delivery thru the sheath, protecting the needle from skiving the inner surface of the sheath while being delivered to the target location.

Other advantages will be apparent from the description that follows, including the figures and claims.

BRIEF DESCRIPTION OF THE DRAWINGS

FIGS. 2(A)-(G) illustrates side schematic views of a transseptal access system according to an implementation of the present invention, showing steps of the use of the system in penetrating a septum.

DETAILED DESCRIPTION

Implementations of the device and method include a device that can be advanced to a septum, e.g., towards a FO. In this exemplary implementation, instead of applying positive pressure to "tent" the FO toward the LA, a negative pressure is applied to a lumen within the sheath, e.g., within an elongated member slidable within the sheath, via a negative pressure source such as a syringe on the proximal end of the sheath. This results in the FO pulling inward. The sheath employs a stationary needle-like central core component contained within the lumen of the sheath that punctures the FO when the same is pulled passed it by the negative pressure. The stationary needle-like central core component may be hollow and may form a portion of the elongated member or may be coupled to a distal end thereof.

After the puncture occurs, a guidewire may be threaded through the puncture and into the LA. The negative pressure creates a stable base for the TS puncture to occur. Moreover, by reversing the prior art process (by pulling the FO past the needle contained within the sheath), the chance of perforation is significantly reduced if not eliminated during TS procedures. In an alternative embodiment, the design may also incorporate ultrasound or other technology within the funnel shaped structure to enable better visualization of the FO prior to the puncture process to further eliminate perforation of adjacent structures. A pressure sensor located at the tip of the needle-like feature may also provide real-time feedback to the user to verify TS access has been achieved. The same may also provide information regarding the level of tension on the FO. Furthermore, a ring of electrodes affixed to the rim of the funnel feature configured in a uni-polar and or bi-polar configuration may also be adapted to further assist alignment and tissue contact of the device prior to crossing the septum. The device may be of a fixed curve (in a number of sizes and radii of curvature) or steerable sheath design and may include variations in length and diameter for various applications.

Figure 1:
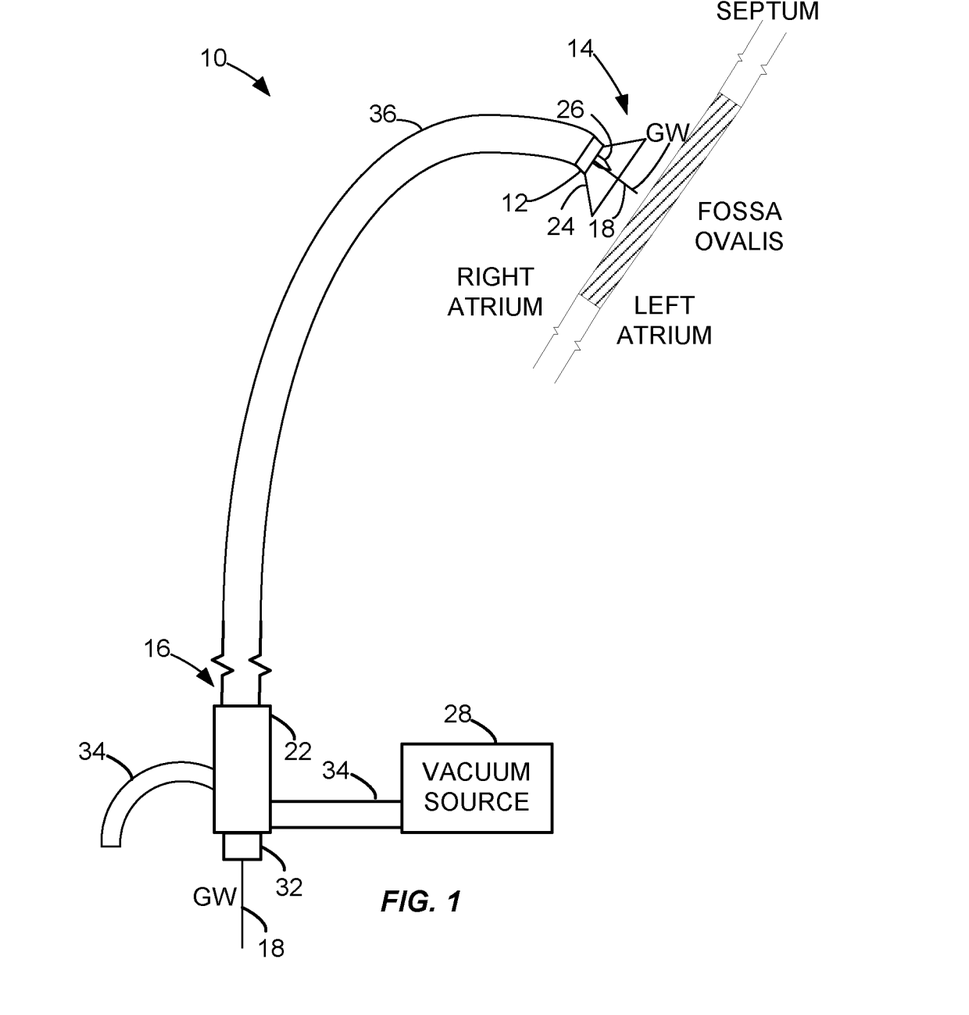
FIG. 1 illustrates a schematic view of a transseptal access system according to an implementation of the present invention.
Figure 2:
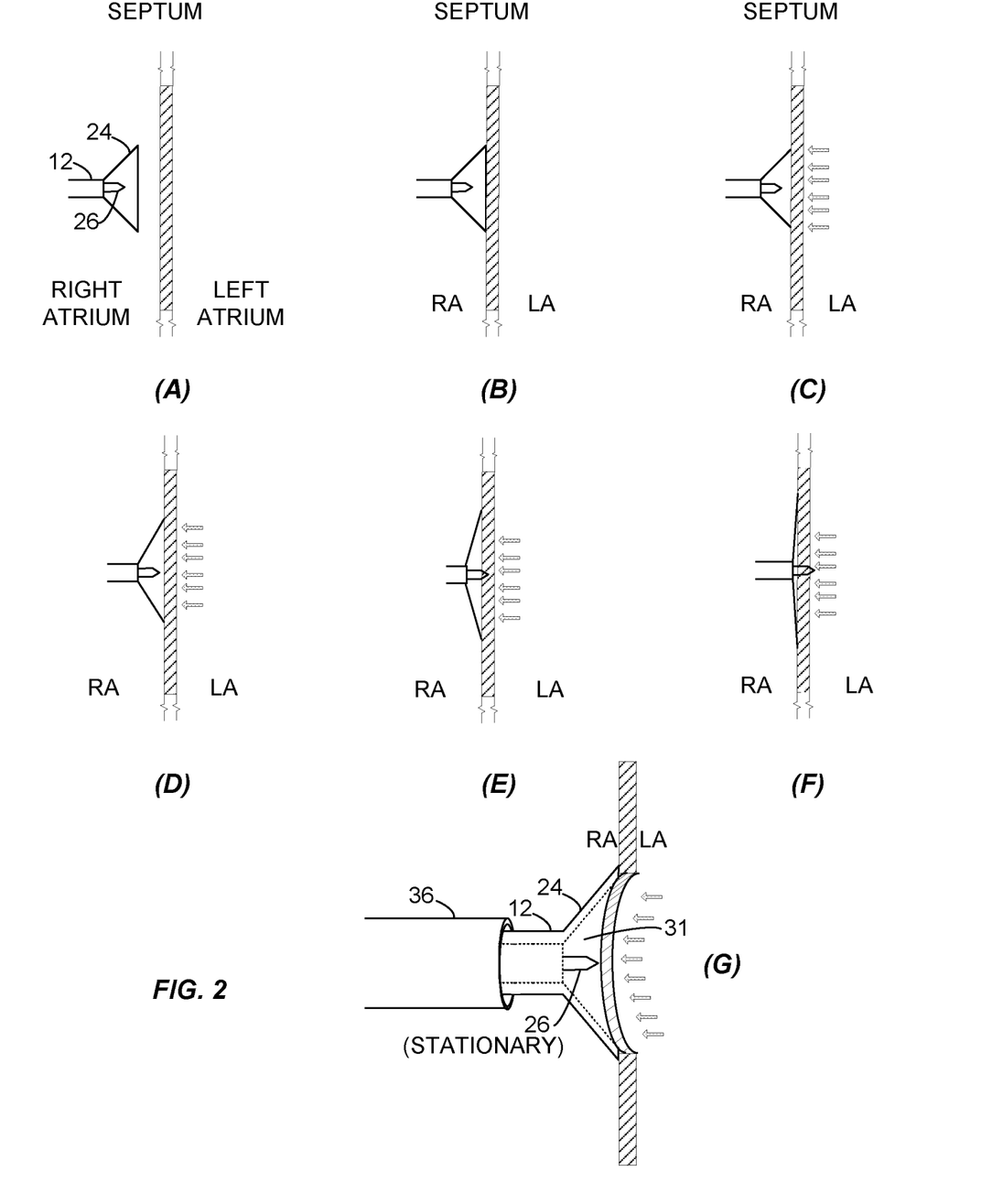

FIG. 1 illustrates one implementation of the current device. A device 10 has a proximal end 16 and a distal end 14. The device 10 includes a funnel 24 extending from an elongated member 12 that slides within a standard TS sheath 36. The TS sheath 36 may be, e.g., an 8 French sheath. In FIG. 1, the funnel is shown in an expanded configuration. However, when within the sheath 36, the funnel is in a retracted configuration. In use, the funnel 24 is configured to engage a FO using a source such as a syringe at the proximal end 16 of the device. A negative pressure or vacuum is drawn to pull in the FO to the piercing element or needle 26, enabling access to the LA. That is, the FO is pulled toward the piercing element or needle and eventually the FO is pulled past the piercing element or needle, causing the piercing element or needle to penetrate the FO. It is noted that the piercing element or needle may be stationary with respect to the sheath, the guide wire, and/or the remainder of the heart. It is the FO that may be caused to move in a direction so as to be penetrated by the piercing element or needle; the FO need not be actively penetrated by a moving needle or piercing element.

FIG. 2(A)-(F) illustrate the above movement of the funnel 24 and FO of the septum past the stationary needle or piercing element 26 and elongated member 12, which may be generally a catheter main body polymer tubing. In (A), the device is situated away from the septum, but the funnel has been extended past the sheath and thus is in a flared or expanded configuration. In (B), the device abuts the septum, but no negative pressure has yet been drawn. In (C), a negative pressure or vacuum begins to pull on the septum, e.g., the FO, such as by a syringe or pump which is in pressure communication with an interior 31 of the funnel. In (D), the negative pressure increases, and the funnel 24 begins to flare out even more. It is noted in this regard that in FIG. 2(A)-(F), the movement of the septum is not shown; it is however shown in FIG. 2(G). In (E), the funnel 24 flares out even more as the septum is pulled towards the needle, and in this figure the needle or piercing element 26 begins to pierce the septum. In (F), the FO has completely moved past the needle 26 because of the applied negative pressure. As noted above, FIG. 2(G) illustrates schematically the movement of the septum, e.g., the FO, towards the stationary needle 26, as a result of the drawn negative pressure.

Figures 3, 4, 5:
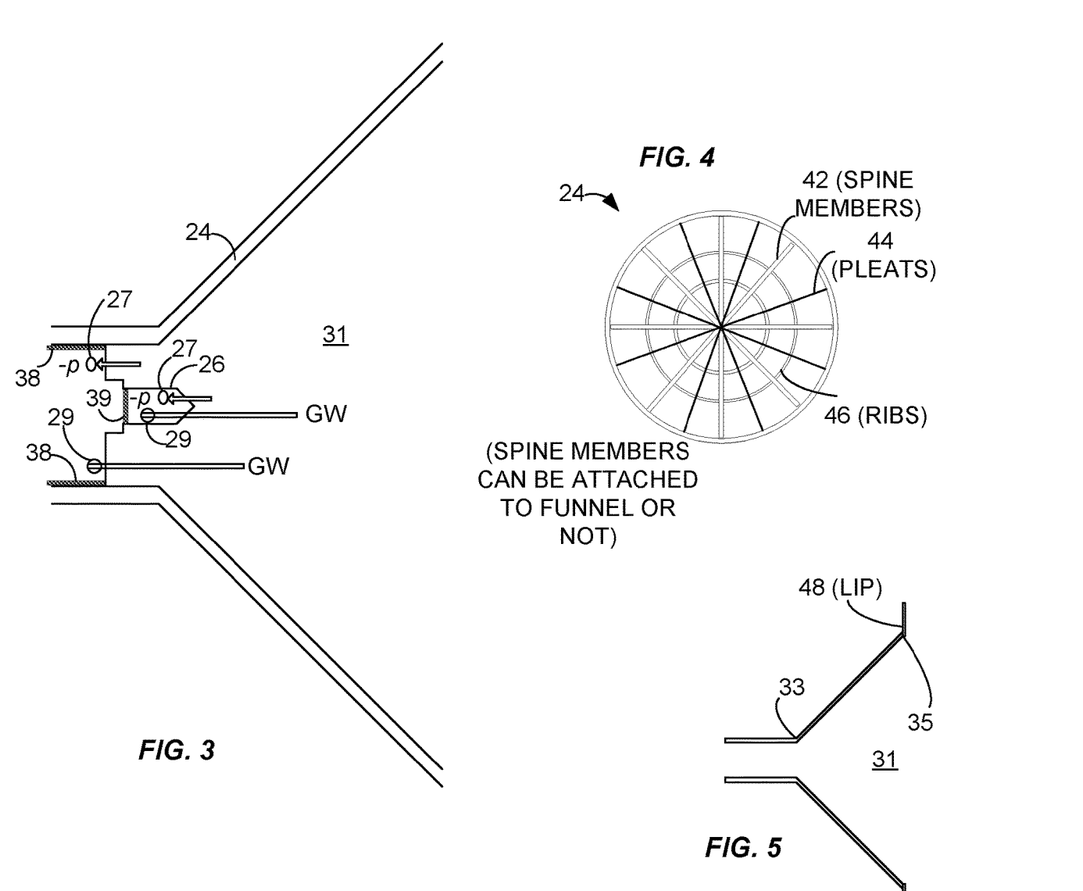
FIG. 3 illustrates a side schematic view of a transseptal access system according to an implementation of the present invention, particularly showing exemplary locations through which negative pressure may be applied, as well as guidewire lumen locations.
FIG. 4 illustrates an end-on view of a of a transseptal access system according to an implementation of the present invention, showing spine members, pleats, and ribs.
FIG. 5 illustrates a side schematic view of a transseptal access system according to an implementation of the present invention, showing a lip providing an enhanced coupling to the septum of some patients.

FIG. 3 illustrates additional details of the distal tip of the elongated member 12, including the funnel 24. In particular, the distal tip 14 of the elongated member 12 is illustrated with the funnel 24 in the expanded configuration. The funnel may be seen to be coupled to the elongated member 12 by virtue of a bond 38. Another bond 39 may be employed to attach the needle or piercing element 26 to the distal tip 14 of the elongated member 12.

Negative pressure may be drawn by one or more vacuum or pressure lumens 27, while one or more guide wire lumens 29 may be employed to pass a guide wire, e.g., into the LA of the heart. Of course, it will be understood that in any given implementation only one guide wire lumen may be required. One or more pressure lumens may be employed to draw the negative pressure, pulling the septum past needle or piercing element 26.

Referring back to FIG. 1, a hemostasis valve 32 may be employed to seal the handle, so as to allow a vacuum and yet enable the user to advance and retract the guide wire during use. A handle 22 is located on the proximal end of the TS access device. A side port tube 34 and syringe hub may be connected to the handle, providing fluid exchange with the inner lumens of the TS access device. Such facilities allow the user to aspirate the lumen to create a vacuum against the septum of the heart, e.g., at the FO, or at other locations along the septum.

Referring to FIG. 4, an end-on view is illustrated of the funnel 24. A number of elements may be employed to enhance the structural integrity of the funnel 24, although not all elements need be employed in every situation, and in many cases no such elements may be employed. First, to assist in the flaring of the funnel, spine members 42 may be employed. The spine members 42 may be attached to the funnel or not, but in any case provide a degree of spring action to flare or fan out the funnel when the same is outside of the sheath. A number of pleats 44 may be employed, the same allowing the funnel to flare out. A number of circumferential ribs 46 may also be employed to assist in the shaping of the flared funnel 24, and these ribs 46 are further discussed below. The spine members and rib members may be made of nitinol wire. However, the polymer of the funnel alone may be designed so as to have memory as well and/or an inherent geometric shape, which may incorporate the pleats noted above, to help the polymer funnel element to deploy into the funnel shape.

In FIG. 4 it is noted that the funnel may be of a soft durometer polymer and can include an additive providing a radio-opaque feature for visualization under fluoroscopy. The flared tip may be soft, thin-walled, and designed to prolapse during application of vacuum, allowing the FO to be forced into contact with the piercing element or needle. In another implementation, the needle may be attached to a mechanism that can be advanced following vacuum application to the FO allowing a controlled perforation of the septum.

As noted above, the piercing element or needle may be bonded to the inside surface of the TS access device. The piercing element or needle may be of a hollow design. After the puncture of the septum occurs, a guidewire can then be advanced through the hollow piercing element or needle through guidewire lumen 29, and advanced into the LA thru the puncture provided.

FIG. 5 illustrates that the funnel 24 may have a lip 48 disposed at a distal end thereof, the lip circumferentially surrounding the funnel 24. The lip 48 provides an even greater attachment of the funnel 24 to the septum. This figure also shows the proximal end 33 and a distal end 35 of the funnel 24.

Figure 6:
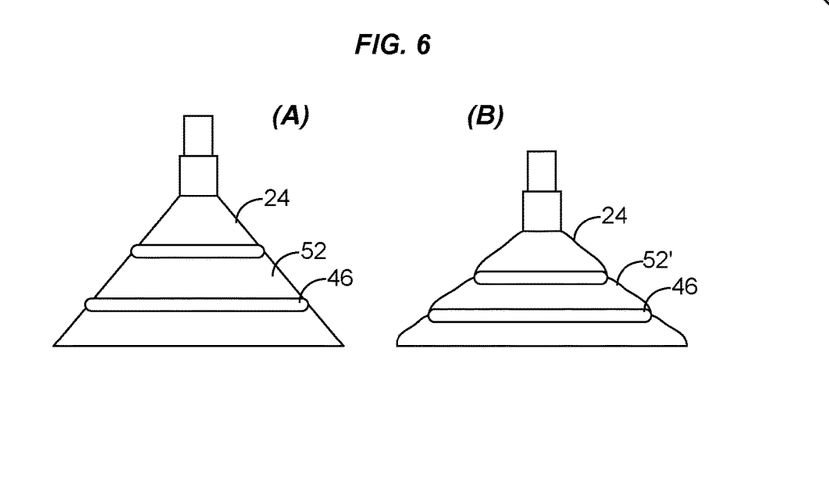
FIG. 6(A)-(B) illustrate side views of a ribbed funnel, illustrating straight sides (A) and convoluted sides (B). Other types of funnels may also be employed.

FIG. 6(A)-(B) illustrate that the funnel 24, including ribs 46, may have a straight conical profile 52 or may have a convoluted profile 52'. In some implementations, the convoluted profile 52' allows for easier folding into the sheath 36 as well as enhanced attachment to the septum.

Figure 7:
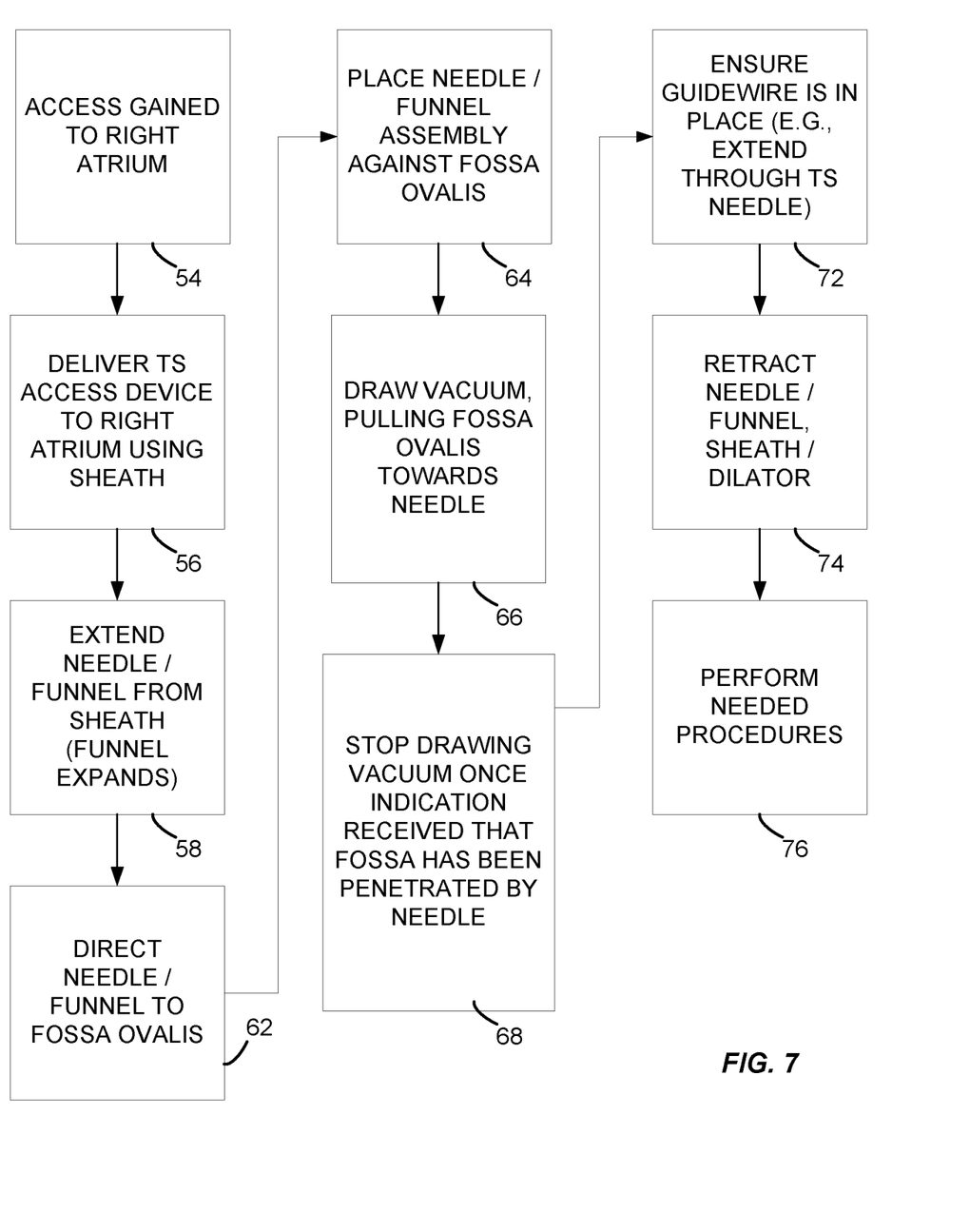
FIG. 7 is a flowchart illustrating a method according to an implementation of the present invention.

FIG. 7 illustrates a flowchart embodying a method of the invention. In a first step, access is gained to the right atrium (step 54). In this step, a femoral or other vein is accessed, allowing movement of devices towards the heart and into the right atrium through the inferior vena cava. A next step is to deliver the TS access device to the right atrium using a sheath (step 56). The needle and funnel are extended from the sheath, causing the funnel to expand by virtue of its own memory element, memory metal in spine or other members, or both. A next step is that the needle and funnel are directed towards the septum, and commonly towards the FO (step 62). A next step is the placement of the needle and funnel assembly against the FO (step 64). A next step is to draw a vacuum or negative pressure, pulling the FO towards the needle (step 66). The vacuum or negative pressure may be drawn using any of the methods described above, including by use of a syringe or micro pump. A next step is to stop the negative pressure drawing once an indication has been received that the FO has been penetrated by the needle (step 68). The indication may be by the detection of the presence of blood in the lumen that draws the negative pressure, a reduction in the measured negative pressure, or the like. Where a reduction in the negative pressure is used, a measurement device may be employed to measure the pressure during the drawing step. A next step is to ensure that a guide wire is in place, e.g., by extending the same through the needle (step 72). A next step is to retract the needle and funnel, as well as the sheath and any dilator that may have been used (step 74). The procedures requiring TS access may then be performed (step 76).

The device significantly improves the safety profile of such procedures, simplifies the same, and reduces the time needed to achieve LA access.

Figure 8:
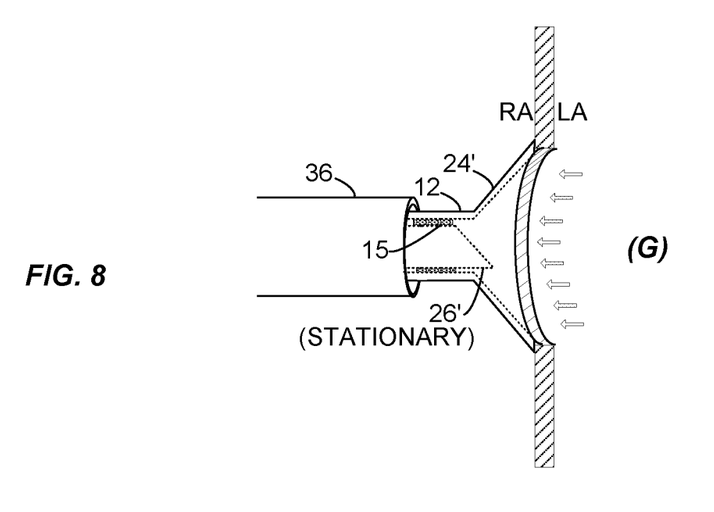
FIG. 8 illustrates a side schematic view of another transseptal access system according to an implementation of the present invention.

In another implementation, shown in FIG. 8, a portion of a needle 26' may be embedded into a semi-flexible tubular element similar to a dilator. In this implementation, a portion of a long needle, which may be similar to a BB needle, has a flexible polymer 24' affixed to its distal portion. The distal end portion polymer portion 24' is affixed to the outer curved portion of a needle by bonds 15 and, during use in the body, the portion 24' deploys into a funnel-like shape.

Certain manufacturing details are now described. The needle may also have a proximal end on which is disposed a luer fitting for a syringe. The tapered or funnel-shaped polymer portion affixed to the distal end may incorporate pleats, such as on some balloons, to help impart a fold during insertion and withdrawal of the device. Furthermore, during insertion and withdrawal of the device, the polymer distal portion may extend past the needle tip and, with the pleats, fold around the distal tip of the needle, protecting the needle from skiving the inner surface of the sheath during movement through the sheath while being inserted into the body.

The prolapsed orientation of the funnel 24 during partial retraction into the sheath 36 enables the inner core to perform as a typical dilator. The tapper portion of the dilator used in a similar way to the dilator of a traditional TS sheath sends tactile information to the proximal end of the dilator where the end-user, grasping the proximal end, can feel the dilator and sheet moving along the septum onto the location of the FO. Furthermore, with the funnel 24 partially extending from the distal end of the sheath, this creates a tapered geometry similar to the traditional dilator, enabling the tapered portion to gradually access the puncture site made by the needle 26. The funnel also provides a positive stop for the needle, thereby acting as a safety feature, preventing the through—and—through perforation common to traditional TS access devices.

After insertion and attainment of the target location, the needle is deployed thru the distal tip of the device. The polymer distal portion may then deploy like an inside-out umbrella against the septal tissue. The needle may be located slightly back from the deployed plane of the polymer funnel portion. Then, using a syringe, a vacuum, suction effect, or other negative pressure between the funnel polymer portion and tissue allows the soft flexible polymer portion to flatten out, pulling the septal tissue inward toward the needle and piercing the septal wall for access to the LA.

Aspects of certain implementations follow.

In some implementations, the funnel is flexible and can flatten substantially perpendicularly to the axis of the lumen of the catheter shaft. In some implementations, when the distal end is flattened against the septum, exposing the tip of the needle-like element, the same extends at least 1 mm past the planar surface of the flattened portion of the funnel-shaped distal end. The funnel may be mechanically capable of flattening by advancing the catheter forward or by creating a negative pressure with the use of a syringe. The needle element may employ a tapper, the tapper being sharp enough to penetrate cardiac tissue. The funnel-shaped distal segment may have a range of angularity from 90 to 180 degrees. In another implementation, the funnel distal portion could be attached to a needle, a dilator or a sheath. In some implementations, the distal portion of the device may employ a pressure transducer to measure cardiac pressure and pressure changes, to define when TS access is achieved. In some implementations, a device is provided such that the distal portion of the device employs an ultrasound element capable of visualizing TS access locations prior to puncture of the FO.

In some implementations, a device is provided where the needle-like element is attached to a tubular element that is advanced distally or proximally by the use of a knob located at the handle of the device. In some implementations, a device is provided having a flexible distal portion to enable steering via a mechanical mechanism located at the handle of the device. In some implementations, a device is provided having a proximal end that includes a handle element having a mechanical slide connected to a tubular structure and a needle or piercing element located at the distal tip, enabling movement in a distal and proximal direction. A proximal end may have a handle that includes a haemostatic valve (e.g., a Merit Medical Passage hemostasis valve (pin 500066)) for guidewire insertion and a luer port (e.g., a Qosina Male Touhy Borst (pin 60343)) to connect a syringe. The hemostasis valve enables insertion of a guidewire or other device and prevents blood from exiting the handle. The sheath portion of the device may employ a fixed curve or may be configured to enable deflection via a steering mechanism at or adjacent to the handle. In this way, the device may be more conveniently directed to a particular location. Where the device employs a fixed curve, a number of difference radii of curvature devices may be provided for use.

In some implementations, a device is provided that, following access to the LA, can be used to deliver contrast to the LA via a syringe through a luer fitting situated on the proximal end of the device, for the purposes of performing venograms.

In some implementations, the cutting element may be slightly off axis and may extend past the surface defined by the lip. In some implementations, a governor or other means may be implemented to inhibit movement of the cutting element past a pre-specified point. In this way, a significant safety factor is added. The mechanism that pushes the needle may be similar to those used to extend the point of a ball point pen (and to retract the same as well).

The elongated member may be a modified dilator. The cone may be fabricated from Sorta-Clear 40A silicone, and may be bonded to the modified dilator using a bond with RTV.

As noted above, variations may be seen especially in the features of the funnel. For example, the funnel may be folded by collapsing in steps, as caused by ribs, so as to allow for easier folding. The wall of the funnel may have a relatively constant thickness, or may have a varying thickness. It has been found that particularly good results are obtained where the wall thickness incorporates a taper, e.g., becomes thinner in the distal direction. In the manufacturing implementations of the invention, a catheter section may be bonded to a cylindrical section mounted to the funnel.

Figure 9:
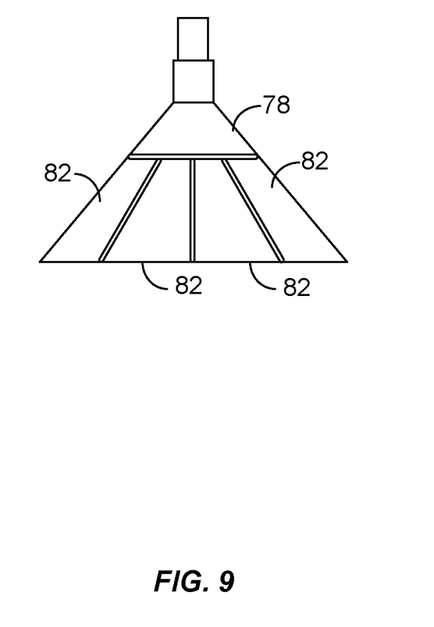
FIG. 9 illustrates a view of a funnel including a partial funnel with multiple segments.

Other variations of these designs will also be seen. For example, in some cases it has been found both sufficient and efficient to replace a full funnel with one in which a partial funnel 78 (see FIG. 9) extends partway distally while multiple segments 82 extend distally from the partial funnel to the distal end. In a specific implementation, eight such "fingers" extend from the partial funnel to the distal end, similar to the tentacles of an octopus. This embodiment has the advantage that the same is easy to fold for insertion (as less folding is required), while still being capable of forming a sufficient negative pressure to pull the septum towards the needle and vice-versa. In this connection it is noted that one negative pressure that has been found sufficient is that drawn by retraction of a syringe, e.g., in the range of 10 to 20 cc. In this or in other implementations, the funnel may be deployed by having the same heat shape set, e.g., with a memory alloy having an AF temperature range of 10 to 25° C. And as mentioned before, the guidewire can allow for multiple deployments of treatment devices following the septal puncture. Treatment devices may even be loaded in a cartridge system for multiple easy deployments, where the cartridge system may be mated to the guidewire. Other inventions will also be apparent to one of ordinary skill in the art, given this teaching.

Other variations of these designs will also be seen. For example, in some cases it has been found both sufficient and efficient to replace a full funnel with one in which a partial funnel extends partway distally while multiple segments extend distally from the partial funnel to the distal end. In a specific implementation, eight such "fingers" extend from the partial funnel to the distal end, similar to the tentacles of an octopus. This embodiment has the advantage that the same is easy to fold for insertion (as less folding is required), while still being capable of forming a sufficient negative pressure to pull the septum towards the needle and vice-versa. In this connection it is noted that one negative pressure that has been found sufficient is that drawn by retraction of a syringe, e.g., in the range of 10 to 20 cc. In this or in other implementations, the funnel may be deployed by having the same heat shape set, e.g., with a memory alloy having an AF temperature range of 10 to 25° C. And as mentioned before, the guidewire can allow for multiple deployments of treatment devices following the septal puncture. Treatment devices may even be loaded in a cartridge system for multiple easy deployments, where the cartridge system may be mated to the guidewire. Other inventions will also be apparent to one of ordinary skill in the art, given this teaching.

The invention claimed is:

1. A device for transseptal access, comprising:
   an elongated member having a proximal end and a distal end; and
   a funnel coupled to the elongated member at the distal end of the elongated member, the funnel having a straight shape or a convoluted shape, the funnel having a proximal end with a first radius and a distal end with a second radius, the funnel having a retracted configuration and an expanded configuration, the expanded configuration defining an interior, the second radius greater than the first radius when the funnel is in the expanded configuration;
   such that the elongated member and the funnel are configured to be delivered to a septal location; and
   such that the funnel is configured to transition from the retracted configuration to the expanded configuration, the expanded configuration being a use configuration; and
   further comprising a pressure lumen associated with the elongated member configured to transmit a negative pressure from a proximal end of the elongated member to the interior of the funnel to create a suction effect to hold the funnel against the septum of the heart, and further comprising a piercing element configured to pierce the septum of the heart when the suction effect is holding the funnel against the septum of the heart, wherein the piercing element is stationary.

2. The device of claim 1, wherein the piercing element is attached to a tubular element that moves within the elongated member.

3. The device of claim 1, wherein the piercing element is coupled to the elongated member.

4. The device of claim 3, wherein in the retracted configuration, the funnel substantially surrounds the piercing element.

5. The device of claim 3, wherein in the expanded configuration, the funnel distal end extends further in a distal direction than does the piercing element.

6. The device of claim 1, wherein in the expanded configuration, the funnel distal end extends further in a distal direction than does the piercing element.

7. The device of claim 1, wherein the piercing element is a dilator with a sharp tip.

8. The device of claim 7, further comprising a fitting attached to the pressure lumen, the fitting configured to attach a negative pressure source thereto.

9. The device of claim 8, wherein the fitting is configured to attach a syringe thereto.

10. The device of claim 8, wherein the negative pressure source is configured to draw a negative pressure of between about that drawn by a 5 cc syringe and that drawn by a 100 cc syringe.

11. The device of claim 10, wherein the negative pressure source is configured to draw a negative pressure of between about that drawn by a 10 cc syringe and that drawn by a 20 cc syringe.

12. The device of claim 1, further comprising a mechanical mechanism configured to enable steering.

13. The device of claim 1, wherein the first radius is between about 3 French to 10 French and the second radius is between about 2.5 mm and 15 mm.

14. The device of claim 13, wherein the first radius is between about 5 French to 8 French and the second radius is between about 5 mm and 10 mm.

15. The device of claim 1, further comprising a rib or spine member, or a lip, attached to the funnel.

16. The device of claim 1, wherein the elongated member has further defined a guidewire lumen therein, the guidewire lumen extending from the proximal end and into the interior of the funnel.

* * * * *